US009844224B2

(12) United States Patent
Jia et al.

(10) Patent No.: US 9,844,224 B2
(45) Date of Patent: Dec. 19, 2017

(54) BITTER ALKALOID CONTAINING CONSUMABLES COMPRISING BITTER BLOCKERS

(75) Inventors: Zhonghua Jia, Cincinnati, OH (US); Kimberley Gray, Loveland, OH (US); Rajesh Venkata Potineni, Cincinnati, OH (US)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 12/993,542

(22) PCT Filed: May 19, 2009

(86) PCT No.: PCT/CH2009/000162
§ 371 (c)(1),
(2), (4) Date: Nov. 19, 2010

(87) PCT Pub. No.: WO2009/140784
PCT Pub. Date: Nov. 26, 2009

(65) Prior Publication Data
US 2011/0086138 A1    Apr. 14, 2011

Related U.S. Application Data

(60) Provisional application No. 61/055,587, filed on May 23, 2008.

(51) Int. Cl.
| A23L 1/226 | (2006.01) |
| A23L 1/302 | (2006.01) |
| A23L 2/56 | (2006.01) |
| A61K 31/522 | (2006.01) |
| A23F 5/46 | (2006.01) |
| A23F 3/40 | (2006.01) |
| A23L 2/52 | (2006.01) |
| A23L 27/00 | (2016.01) |

(52) U.S. Cl.
CPC .............. *A23F 5/465* (2013.01); *A23F 3/405* (2013.01); *A23L 2/52* (2013.01); *A23L 27/86* (2016.08)

(58) Field of Classification Search
CPC ........ A23V 2250/25; A23V 2250/2108; A23L 1/22083
USPC ........................................................ 426/534
See application file for complete search history.

(56) References Cited

U.S. PATENT DOCUMENTS

| 3,087,821 A | 4/1963 | Horowitz et al. |
| 3,429,873 A | 2/1969 | Horowitz et al. |
| 3,653,923 A | 4/1972 | Ushii et al. |
| 3,739,064 A | 6/1973 | Rizzi |
| 3,821,417 A * | 6/1974 | Westall et al. ............ 426/3 |
| 3,857,962 A | 12/1974 | Westall et al. |
| 3,934,047 A | 1/1976 | Schade |
| 3,984,394 A | 10/1976 | Westall et al. |
| 4,154,862 A | 5/1979 | Guadagni et al. |
| 4,826,824 A * | 5/1989 | Schiffman ............... 514/47 |
| 6,165,516 A | 12/2000 | Gudas et al. |
| 7,815,965 B2 | 10/2010 | Edwards et al. |
| 2002/0188019 A1 | 12/2002 | Ley et al. |
| 2007/0116821 A1 | 5/2007 | Prakash et al. |
| 2007/0116825 A1 | 5/2007 | Prakash et al. |
| 2007/0116834 A1 | 5/2007 | Prakash et al. |
| 2008/0227867 A1 | 9/2008 | Ley et al. |

FOREIGN PATENT DOCUMENTS

| CH | 592418 A5 | 10/1977 |
| EP | 1972203 A1 | 9/2008 |
| GB | 1428945 A | 3/1976 |
| WO | 2007061908 A1 | 11/2006 |
| WO | 2007061898 A1 | 5/2007 |
| WO | 2008148239 A1 | 12/2008 |

OTHER PUBLICATIONS

Qin, X.-D., Liu, J.-K. 2003. A New Sweet Dihydrochalcone-Glucose from Leaves of Lithocarpus pachyphyllus (Kurz) Rehd. (Fagaceae). Z. Naturforsch. vol. 58c. pp. 759-761.*
Drewnowski, A., Gomez-Carneros, C. 2000. "Bitter taste, phytonutrients, and the consumer: a review." Am. J. Clin. Nutr. vol. 72. pp. 1424-1435.*
Friedman, M., Kim, S.-Y., Lee, S.-J., Han, G.-P., Han, J.-S., Lee, K.-R., Kozukue, N. 2005. "Distribution of Catechins, Theaflavins, Caffeine and Theobromine in 77 Teas Consumed in the United States." J. Food Sci. vol. 70. pp. C550-0559.*
"Masking the bitter taste of pharmaceuticals." Jul. 2000. Manufacturing Chemist. pp. 16-17.*
Guadagni, D.G. Maier, V.P. Turnbaugh, J.G. 1974. "Some Factors Affecting Sensory Thresholds and Relative Bitterness of Limonin and Naringin." J. Sci. Fd. Agric. vol. 25, pp. 1199-1205.*
Guadagni, D.G., Maier, V.P., Turnbaugh, J.G. 1974. "Effect of Subthreshold concentrations of Limonin, Naringin and Sweeteners on Bitterness Perception." J. Sci. Fd. Agric. vol. 25, pp. 1349-1354.*
XP-002495727, H. Van Gorsel, et al., "Compositional Characterization of Prune Juice", Journal of Agricultural and Food Chemistry, vol. 40, No. 5, pp. 784-789.
XP-002333457, N. Artkin et al., "HPLC Determination of Phenolic Compound and Procyanidin Content of Turkish Apple Juice Concentrate", FSTA, 1998, ISBN 2-7380-0728-7, J. Journal, vol. 22, No. 5, pp. 327-335.
XP-002495728, T. E. Furia (Editor), "CRC Handbook of Food Additives", vol. 2,1980, CRC Press, Boca Raton, US.
M. M. Petkovsek, et al., "Parameters of Inner Quality of the Apple Scab Resistant and Susceptible Apple Cultivars (Malus Domestica Borkh.)", Scientia Horticulture, vol. 114,No. 1, pp. 37-44, Aug. 18, 207, ISSN: 0304-4238.
IGOE, Dictionary of Food Ingredients, 5th Edition, p. 190, Jun. 2011.
IGOE, Dictionary of Food Ingredients, 3rd Edition, 1996.

* cited by examiner

*Primary Examiner* — Nikki H Dees
(74) *Attorney, Agent, or Firm* — Norris McLaughlin & Marcus PA

(57) ABSTRACT

Disclosed are bitter alkaloid-containing consumables comprising bitter blockers for a reduced alkaloid-derived bitterness and methods of forming said consumables.

26 Claims, No Drawings

BITTER ALKALOID CONTAINING CONSUMABLES COMPRISING BITTER BLOCKERS

This is an application filed under 35 USC 371 of PCT/CH2009/000162.

This is a Provisional Application for Patent pursuant to 35 U.S.C. §111(b).

TECHNICAL FIELD

Disclosed are compositions and consumables which comprise one or more alkaloid bitterness providing ingredient and one or more bitter blocker to reduce the alkaloid bitter taste, and methods of forming said compositions and consumables.

BACKGROUND

Bitter blocking or masking, i.e. the reduction of bitter taste, is of great interest in the food and pharmaceutical industries to render foods or medicines more palatable to the consumer/patient. Bitter taste in general is undesirable, though some types or components of bitter tastes (for example, some bitter components in coffee, chocolate, beer, grapefruit etc.) are desired.

Bitter compounds encompass a wide structural range of different chemical classes, however, slight structural changes including isomeric or enantiomeric forms can strongly influence the bitter taste detection threshold as well as completely alter the overall taste profile (for example, L-tryptophan is bitter while its D-enantiomer is distinctly sweet, hesperidin is tasteless but the positional isomer neohesperidin is strongly bitter). Some classes of bitter compounds include simple salts such as sodium sulfate, peptides, polyphenols, terpenoids, flavonoids, alkaloids, and many more. Examples of bitter alkaloids are caffeine and nicotine.

Unlike other tastes, there are a larger number of different bitter taste receptors that are able to detect bitter taste. Some will bind to structurally diverse bitter compounds, some are very specific. Taste cells usually comprise more than one bitter taste receptors but not all of them. It is believed that different kinds of bitter qualities are distinguishable, and some are more tolerable than others, or even desirable.

A bitter blocker should ideally be selective for bitter taste to some degree and not, or only slightly, influence the other basic taste qualities (sweet, sour, salty, umami). It should block the undesirable bitterness of one or more bitter ingredient, for example caffeine or other undesirable alkaloid bitter ingredients found in various botanicals (for example, without limitation, coffee, chocolate, guarana, kola nuts and other botanicals that comprise one or more of caffeine, theobromine and theophylline), but should not block, or at least not completely block, desired types of bitterness, for example the bitter taste notes typical of coffee and chocolate, or their aroma.

The complex situation involving a large number of bitter receptors as well as a structurally extremely wide range of bitter ligands that are not consistently recognised by bitter receptors is increased in complexity by different bitter phenotypes in humans. Cell-based screens often achieve results that cannot be reproduced in sensory experiments. Accordingly, bitter blockers are usually discovered by trial and error in sensory evaluations using human test subjects.

The bitterness of certain alkaloids is known to be reduced by a variety of substances, in particular, caffeine is often used as a bitter test substance and its bitterness is known to be reduced by a great number of compounds or complex mixtures. A strongly sweet tasting mixture that reduces caffeine bitterness is, for example, erythritol-CaHPO4, L-glutamic acid, inosinic acid and 5-ribonucleotides.

Furthermore, chitosan is able to reduce caffeine bitterness but is strongly astringent and has been described as "mouth-puckering". The mechanisms of caffeine bitter-blocking is not known, but is probably caused to a large part by camouflage through strong flavours, in particular strong sweet flavors or off-tastes, limiting their applicability. Certain plant stanol esters, fatty acids and edible oils are known to lower caffeine bitterness but tend to effect the other taste qualities as well and add fat to the food product which may not be practical. Ferulic acid adds its own distinct taste when reducing caffeine bitterness. Pyridinium glycinyl betain, while tasteless on its own, was found to reduce the bitterness of the alkaloid caffeine as well as the aminoacid L-phenyl-alanine, the Gly-Leu peptide, and the bitter glycosides salicin and naringin. U.S. Pat. No. 4,154,862 describes the bitter reduction of caffeine by neodiosmine. Most known bitter reducing compounds are not able to reduce caffeine bitterness completely, with masking effects usually remaining below 50%, for example neodiosmine, poly-gamma-glutamic acid, cellotrioside, homoeriodictyol, eriodictyol, gamma-amino butyric acid, alpha-alpha-trehalose, taurin, L-theanine, 2,4-dihydroxybenzoic acid, 2,4-dihydroxybenzoic acid N-vanillyl amide, [2]-gingerdione.

There remains a need for alternative or improved alkaloid-bitterness reducing compounds.

Trilobatin and Hesperetin dihydrochalcone 4″-beta-D-glucoside (HDG) are sweeteners that have not been previously described to have alkaloid bitter blocking characteristics.

Trilobatin is a natural dihydrochalcone type sweetener that occurs in the Chinese sweet tea plant *Lithocarpus polystachyus*, the leaves of which have been consumed as sweet tea in the south of China for centuries. It has also been found in the apple species *Malus trilobata*, and from this source the name trilobatin was derived. Trilobatin was first chemically synthesized in 1942 under the name p-phlorizin. Under the name prunin dihydrochalcone, U.S. Pat. No. 3,087,821 described its use as a sweetener in 1963.

Trilobatin has been used as a sweetener in concentrations well above its sweetness detection level, but has not been described to suppress bitterness.

Hesperetin dihydrochalcone 4″-beta-D-glucoside (HDG) is a known sweetener that can be synthesized from hesperidin, which is present in peels/fruit of *Citrus sinensis* L. (Rutaceae), commonly known as sweet orange, and *C. reticulata*, commonly known as tangerine or mandarin. The synthesis of HDG may be performed by reduction of hesperidin in dilute alkali which yields hesperidin dihydrochalcone, followed by partial hydrolysis, either by acid or by a dissolved or immobilized enzyme, to form HDG, for example as described in U.S. Pat. No. 3,429,873. HDG is known to suppress naringin (a flavonoid glycoside) and limonin (limonoid, or rather tetranortriterpenoid) bitterness at high suprathreshold concentration (ratio taste units sweetener to bitter compound at least 2:1, apparently a masking effect through strong sweet taste) but not at concentrations at or below the sweet taste detection threshold of HDG.

HDG has not been known to suppress alkaloid bitterness at any concentration.

SUMMARY

Applicant has discovered that when the bitter blockers of formula (1) described herein (trilobatin and HDG), are used in a concentration of about 0.3 to about 200 ppm in combination with alkaloid bitterness providing ingredients (including, without limitation, caffeine, theobromine, and theophylline), they reduce alkaloid bitterness. At the low end of the concentration at or near their sweetness detection threshold, the bitter blockers have the additional advantage of not altering the flavor profile and not introducing off-tastes (undesirable taste notes, for example, without limitation, metallic taste).

Provided are the following:

(1) A composition comprising
   a) at least 10 mg/l of one or more bitter alkaloid optionally selected from caffeine, theobromine, and theophylline, and
   b) at least one bitter blocker of formula (1),

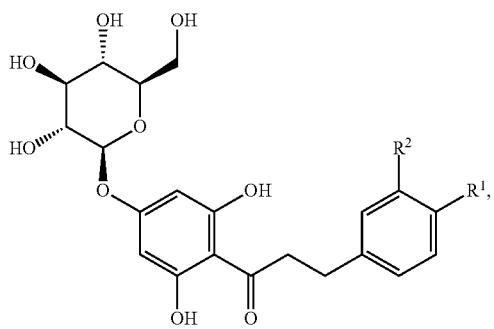

(1)

wherein $R^1$ is selected from the group consisting of OH and $OCH_3$, and $R^2$ is selected from the group consisting of H and OH, $R^1$ and $R^2$ comprise at least one OH group, and when $R^1$ is OH then $R^2$ is H, and when $R^1$ is $OCH_3$ then $R^2$ is OH, and wherein the at least one bitter blocker has a concentration of 0.3 to 200 ppm.

(2) A composition as described herein including the composition of item (1) wherein the bitter blocker of formula (1) is trilobatin and is present in a concentration of 3 to 200 ppm.

(3) A composition as described herein including the composition of item (1) wherein the bitter blocker of formula (1) is hesperitin dihydrochalcone 4"-beta-D-glucoside (HDG) and is present in a concentration of 0.3 to 20 ppm.

(4) A composition as described herein including the compositions of any one of items (1) to (3), wherein one or more ingredients selected from the group consisting of 4-(2,2,3-Trimethylcyclopentyl)butanoic acid, vanilla extracts, licorice extracts, glycyrrhizin, thaumatin, and mixtures thereof are present.

(5) A composition as described herein including the compositions of any one of items (1) to (4) comprising one or more ingredient selected from the group consisting of one or more vitamins provided as an additive; one or more B-vitamins provided as an additive; coffee or an extract thereof (*Coffea* spec.): cocoa or an extract thereof (*Theobroma* spec.); guarana or an extract thereof (*Paugllinia cupana, P. crysan,* or *P. sorbilis*); black tea or an extract thereof, green tea or an extract thereof, yerba mate or an extract thereof (*Camellia* spec. extracts), Yaupon/Cassina extracts (*Ilex vomitoria*); taurine; ginseng or an extract thereof; kola or an extract thereof (*Cola acuminata*); carob or an extract thereof (*Ceratonia siliqua*); maltodextrin; inositol; carnitine; creatine; glucuronolactone; and *ginkgo biloba* extract.

(6) A composition as described herein including the compositions of any one of items (1) to (5) which is a consumable, optionally selected from food, beverage, nutraceutical and pharmaceutical.

(7) A composition as described herein including the compositions of any one of items (1) to (5) which is a beverage comprising caffeine as a bitter blocker.

(8) A beverage consumable as described herein including the beverage consumable of item (7) which is selected from the group consisting of coffee beverage for hot consumption, coffee beverage for iced consumption, cocoa beverage for hot consumption, cocoa beverage for iced consumption, black tea beverage for hot consumption, black tea beverage for iced consumption, green tea beverage for hot consumption, green tea beverage for iced consumption, mate tea beverage for hot consumption, mate tea beverage for iced consumption, energy drink for cold consumption.

(9) A composition as described herein including the compositions of any one of items (1) to (8) comprising trilobatin extracted from a botanical source, optionally selected from parts or leaves of *Lithocarpus polystachyus* (Chinese sweet tea) and parts or leaves of an apple species, said apple species optionally being selected from *Malus trilobata*.

(10) A method of blocking bitterness in consumables wherein 0.3 ppm to 200 ppm of a bitter blocker of formula (1)

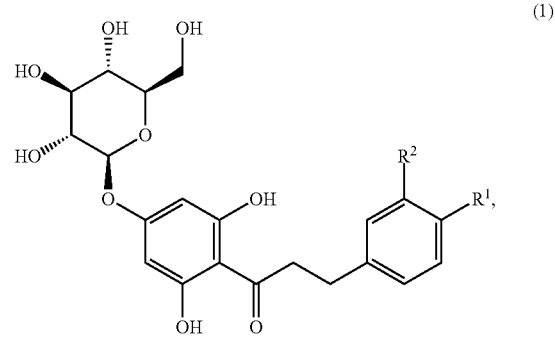

(1)

wherein $R^1$ is selected from the group consisting of OH and $OCH_3$, and $R^2$ is selected from the group consisting of H and OH, and $R^1$ and $R^2$ comprise at least one OH group, are admixed to a consumable or composition for a consumable that comprises at least 10 mg/l of a bitter alkaloid optionally selected from caffeine, theobromine, and theophylline.

(11) A method as described herein including the method of item (10), wherein the bitter blocker trilobatin extracted from a botanical source optionally selected from parts or leaves of *Lithocarpus polystachyus* (Chinese sweet tea) and parts or leaves of an apple species, said apple species optionally being selected from *Malus trilobata* is used.

(12) Use of a bitter blocker of formula (1),

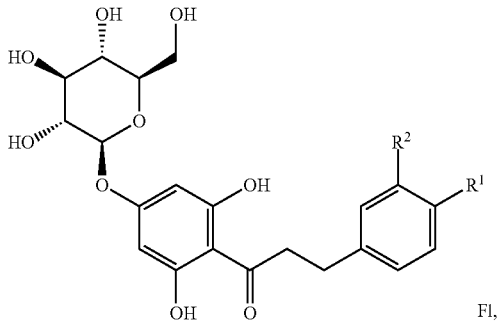

wherein $R^1$ is selected from the group consisting of OH and $OCH_3$, and $R^2$ is selected from the group consisting of H and OH, $R^1$ and $R^2$ comprise at least one OH group, and when $R^1$ is OH then $R^2$ is H, and when $R^1$ is $OCH_3$ then $R^2$ is OH, for the reduction of the bitterness of a bitter alkaloid optionally selected from caffeine, theobromine, and theophylline, in consumables optionally selected from food, beverage, nutraceutical and pharmaceutical.

DETAILED DESCRIPTION

The bitter blocker of formula (1) has the chemical structure as shown below, wherein $R^1$ is selected from the group consisting of OH and $OCH_3$, and $R^2$ is selected from the group consisting of H and OH, $R^1$ and $R_2$ comprise at least one OH group, and when $R^1$ is OH then $R^2$ is H (trilobatin), and when $R^1$ is $OCH_3$ then $R^2$ is OH (HDG).

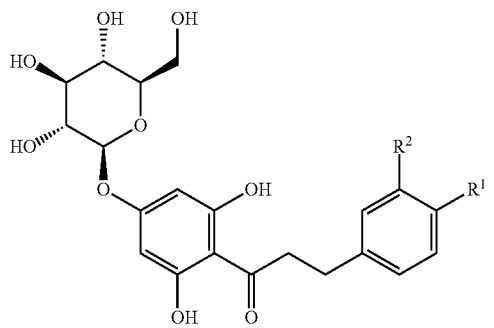

(1)

Bitter blockers of formula (1) include trilobatin ($R^1$=OH, $R^2$=H) and HDG ($R^1$=$OCH_3$, $R^2$=OH).

HDG or hesperitin dihydrochalcone 4″-beta-D-glucoside is also known as 1-[4-(beta-D-glucopyranosyloxy)-2,6-dihydroxyphenyl]-3-(3-hydroxy-4-methoxyphenyl)-1-propanone. The chemical structure of HDG is given below.

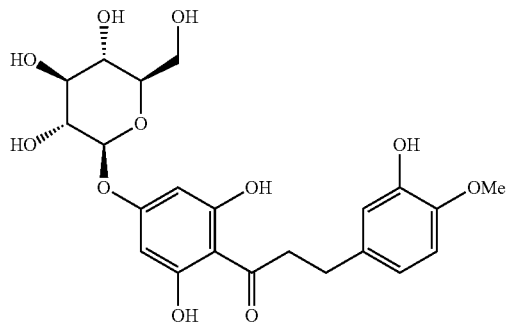 [SMILES: COc1ccc(CCC(=O)c2c(O)cc(O[C@@H]3O[C@H](CO)[C@@H](O)[C@H](O)[C@H]3O)cc2O)cc1O]

Trilobatin or 1-[4-(beta-D-glucopyranosyloxy)-2,6-dihydroxyphenyl]-3-(4-hydroxyphenyl)-1-propanone is also known as p-Phlorizin, Phloretin 4'-glucoside, Phloretine-4'-glucoside, Prunin dihydrochalcone, or p-Phloridzin. Its chemical structure is given below.

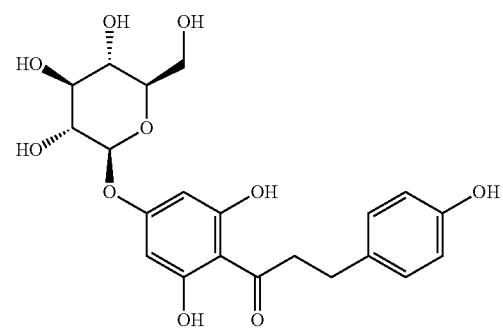 [SMILES: O=C(CCc1ccc(O)cc1)c1c(O)cc(O[C@@H]2O[C@H](CO)[C@@H](O)[C@H](O)[C@H]2O)cc1O]

The sweetness detection thresholds for the bitter blockers were determined by the applicant.

The sweetness detection threshold varies somewhat in different individuals. For example, some individuals are able to detect the sweetness of sucrose in a very low concentration of 0.4%, others need at least 0.7%, or at least 1% or even more. All examples were performed with sweet sensitive panelists able to detect at least 0.5% of sucrose or less. The concentration detectable by the average consumer will therefore be higher.

A concentration near a compound's sweetness detection threshold is defined herein as a concentration with an isointensity to sucrose of up to 1% sucrose or lower, for example, up to 0.8%, up to 0.75%, up to 0.7%, or up to 0.5% sucrose, as detected by sweet sensitive panelists.

The isointensity of various trilobatin concentrations was determined in water, and 100 ppm trilobatin was isosweet to 0.5% sucrose and 200 ppm was isosweet to 1.0% sucrose.

Similarly, the isointensity of various HDG concentrations was determined in water, and 10 ppm HDG was isosweet to 0.5% sucrose, and 20 ppm was isosweet to 1.0% sucrose.

An example of a useful concentration of the bitter blocker near its sweetness detection threshold is 0.3 to 200 ppm, or 0.3 to 150 ppm, or 0.3 to 100 ppm in consumables or compositions.

Compositions, in particular flavor compositions can be formed that comprise the bitter blockers and the bitter alkaloid and optionally food grade excipients, for addition to consumables. Alternatively, the bitter blockers can be directly added to consumables.

For trilobatin, a particularly useful range is 3 to 200 ppm, or 3 to 150 ppm, or 3 to 100 ppm in consumables.

HDG, which has a lower sweet taste detection threshold than trilobatin, tastes sweeter at a lower concentration. For HDG, the threshold is about 10 times less that of trilobatin. Accordingly, particularly useful HDG concentrations that do not alter the flavor profile are towards the lower end of the indicated range, for example, without limitation, 0.3 to 100 ppm, 0.3 to 50 ppm, 0.3 to 20 ppm or 0.3 to 10 ppm in consumables.

The bitter blocker can be used in various consumables which comprise one or more alkaloid bitterness providing ingredient, either naturally or provided as an additive. Said consumables include all food products, including but not limited to, cereal products, rice products, tapioca products, sago products, baker's products, biscuit products, pastry products, bread products, confectionery products, desert products, gums, chewing gums, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, sweeteners, nutraceuticals, gelatins, pharmaceutical and non-pharmaceutical gums, tablets, lozenges, drops, emulsions, elixirs, syrups and other preparations for making beverages, and combinations thereof. Consumables further include nutraceuticals and pharmaceuticals. For example, many medicaments, for example, without limitation, pain mediciations, include caffeine to enhance their effect, and therefore have a bitter taste. Theophylline is a methylxanthine drug used in therapy for respiratory diseases such as COPD or asthma. Nicotine is a bitter methylxanthine drug used in, for example, chewing gum to help to quit smoking.

Groups of consumables of interest include, for example, without limitation, water-based consumables, solid dry consumables and dairy products, dairy-derived products and dairy-alternative products.

Water-based consumables include but are not limited to beverage, aqueous drink, enhanced/slightly sweetened water drink, carbonated beverage, non-carbonated beverage, soft drink, non-alcoholic drink, alcoholic drink, fruit drink, juice, fruit juice, vegetable juice, coffee, tea, black tea, green tea, oolong tea, herbal tea, cocoa (water-based), cocoa (milk-based), cocoa (soy-based), tea-based drink, coffee-based drink, cocoa-based drink, syrup, frozen fruit, frozen fruit juice, water-based ice, dairy ice, fruit ice, sorbet, and beverages formed from botanical materials (whole or ground) by brewing, soaking or otherwise extracting, and beverages formed by dissolving instant powders or concentrates (coffee beans, ground coffee, instant coffee, cocoa beans, cocoa powder, instant cocoa, tea leaves, instant tea powder), and the above-mentioned concentrates.

Solid dry consumables include but are not limited to cereals, baked food products, biscuits, bread, breakfast cereal, cereal bar, energy bars/nutritional bars, granola, cakes, cookies, crackers, donuts, muffins, pastries, confectioneries, chewing gum, chocolate, fondant, hard candy, marshmallow, pressed tablets, snack foods, and botanical materials (whole or ground), and instant powders for reconstitution as mentioned herein above.

Dairy products, dairy-derived products and dairy-alternative products include but are not limited to milk, fluid milk, cultured milk product, cultured and noncultured dairy-based drinks, cultured milk product cultured with *lactobacillus*, yoghurt, yoghurt-based beverage, smoothy, lassi, milk shake, acidified milk, acidified milk beverage, butter milk, kefir, milk-based beverage, milk/juice blend, fermented milk beverage, icecream, dessert, frozen yoghurt, soy milk, rice milk, soy drink, rice milk drink.

Milk includes, but is not limited to, whole milk, skim milk, condensed milk, evaporated milk, reduced fat milk, low fat milk, nonfat milk, and milk solids (which may be fat or nonfat).

Consumables may contain from about 1 to about 3000 mg/kg of a purine alkaloid/methylxanthine, for example, without limitation, caffeine, theobromine, and theophylline (usually less than 300 mg/serving caffeine, which depending on body weight and metabolism may lead to intoxification).

Ranges of methylxanthines (for example, without limitation, caffeine, theobromine, and theophylline) in consumables include, for example, 1 to 3000 mg/kg, 10 to 3000 mg/kg, 10 to 1000 mg/kg, 100 to 1000 mg/kg.

Compositions for consumables may have the same concentrations or may be more concentrated, for use in consumables in diluted form.

For example, liquid decaffeinated coffee has about 20 to 30 mg/l, liquid espresso coffee up to 2200 mg/l or more of caffeine. Soft drinks like cola usually have about 100 to about 200 mg/l caffeine, energy drinks about 300 to about 400 mg/l or higher, for example up to about 800 mg/l or higher.

Bitter alkaloids as herein described include purine alkaloids and methlyxanthines. Caffeine, theophylline, and theobromine are naturally occurring methylxanthines and purine alkaloids.

The structure of a purine alkaloid is shown below. R1, R2 and R3 are selected from H and methyl. R1, R2 and R3 are methyl for caffeine (aka 1,3,7-trimethyl-xanthine), R1 is H and R2 and R3 are methyl for theobromine, and R1 and R2 are methyl and R3 is H for theophylline.

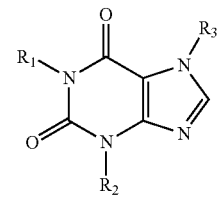

Paraxanthine, or 1,7-dimethylxanthine, is a dimethyl derivative of xanthine.

The bitter alkaloid (for example a purine alkaloid or natural methylxanthine such as, without limitation, caffeine, theobromine, and theophylline) can be naturally present in the consumable, or may be provided as an additive. If provided as an additive in a consumable it may be synthesized chemically, produced by fermentation or enzymatic processes or extracted from natural sources, in particular botanical sources. For example, the seeds of guarana fruits, a prime ingredient of energy drinks, contains large amounts of caffeine. Other sources of methylxanthines include coffee beans, tea leaves (including black, green and mate tea), cocoa beans, carob, guarana berries, and kola nuts.

Alkaloid bitterness providing ingredients as defined herein include purine alkaloids and methylxanthines, including without limitation those occurring in botanical materials, for example, without limitation, one or more of caffeine, theobromine, theophylline, nicotine, and further alkaloid bitter ingredients that are present in botanical materials including, without limitation, coffee beans, cocoa beans, tea leaves (black, green, mate), guarana berries, and kola nuts. The alkaloid bitterness providing ingredient may be present in the consumable in any form including ground beans or leaves or other plant material, or extracts thereof.

Plants that contain a high amount of natural methylxanthines include, without limitation, *Theobroma* spec. (including *Theobroma cacao, Theobroma bicolor, Theobroma angustifolium*) (cocoa beans); *Ilex paraguariensis* (Yerba mate); *Ilex vomitoria* (Yaupon Holly, Yaupon, or Cassina); *Camellia* spec. including *C. sinensis* and *C. oleifera* (tea); *Paullinia cupana* (syn. *P. crysan, P. sorbilis*) (Guarana berries); *Coffea* spec., (including *C. arabica, C. canephora* (aka *C. robusta*), *C. congensis, C. dewevrei, C. excelsa, C. gallienii, C. bonnieri, c. magnistipula, C. mogeneti, C. liberica, C. stenophylla*) (Coffee seeds or beans); *Cola* spec. (including *Cola acuminata*) (kola nuts), *Ceratonia siliqua* (Carob seed pods aka St. John's bread).

In certain products the sweetness detection threshold of compounds of formula (1) will be higher, for example in dairy products, dairy-derived products and dairy-alternative products, Dairy-derived food products contain milk or milk protein. Dairy-alternative products contain (instead of dairy protein derived from the milk of mammals) protein from botanical sources (soy, rice, etc.). For dairy products, dairy-derived products and dairy-alternative products, a useful concentration near the sweetness detection threshold for trilobatin will be from about 10 to 500 ppm or higher, and may be up to 550 ppm, 600 ppm, 650 ppm, 700 ppm, or 750 ppm; for HDG, a useful concentration near the sweetness detection threshold will be from 1 to 50 ppm or higher, and may be up to 55 ppm, 60 ppm, 65 ppm, 70 ppm, or 75 ppm.

Energy drinks are soft drinks comprising caffeine and optional ingredients including, without limitation, vitamins (typically B-vitamins), herbs, and/or other ingredients to increase physical performance and/or mental alertness.

Some examples of optional ingredients for energy drinks, without limitation, are guarana (extracts from the guarana plant), yerba mate, taurine, various forms of ginseng, maltodextrin (a sweetener), inositol, carnitine, creatine, glucuronolactone, and *ginkgo biloba* plant extract. Some energy drinks contain sugars in high concentration, some are artificially sweetened.

Consumables of particular interest are those comprising methylxantines, for example, without limitation, caffeine, theobromine, and theophylline, and/or comprising an ingredient comprising one or more of these alkaloids, for example, without limitation, coffee beans, cocoa beans, guarana, kola nuts or other botanical material, or extracts of any of these materials.

The bitter blocker of formula (1) is usually provided as an additive and can be used in purified or isolated form or in the form of a botanical extract comprising the bitter blocker. For example, trilobatin or HDG can be chemically synthesized, or extracted from a botanical source. For example, trilobatin can be extracted from a botanical source including but not limited to *Lithocarpus polystachus* and *Malus* spp. HDG can be synthezised chemically or starting from hesperidin, which is can be extracted from natural sources, as described herein.

The bitter blocker of formula (1) can be used in a concentration of about 0.3 to about 200 ppm or higher.

Consumables may contain acids to provide a low pH. For example, many beverages have a low pH, for example, from pH 2.6 to 3. Bitter blockers described herein also may work under low pH conditions and show a bitter blocking effect.

The bitter blocker of formula (1) can be combined with optional ingredients that block or mask bitter taste, and/or astringent taste, for example, without limitation, 4-(2,2,3-Trimethylcyclopentyl)butanoic acid, vanilla extracts, licorice extracts, glycyrrhizin, thaumatin, and mixtures of one or more of these ingredients.

Further optional bitter taste masking ingredients can be found, for example, in US20030529814 and WO2006138419, and in Modifying Bitterness: Mechanism, Ingredients and Applications, edited by G. Roy, Technomic Publishing Company, Inc., 1997, Lancaster, Pa.

EXAMPLES

All concentrations in % are % (wt/wt), unless otherwise indicated. A tasting panel of 5 to 8 panelists was asked to compare the bitterness of two samples (sample with trilobatin and control without) of various caffeine-containing consumables.

Different concentrations/ranges were tested, with the ones indicated being the ones with a clear bitter masking effect. While higher concentrations reach a bitter masking effect, panelists found a negative impact on the overall flavor profile at higher concentrations.

Example 1

Reduction of Alkaloid Bitterness in Cocoa with Trilobatin

A tasting panel of 5 to 8 panelists was asked to compare and record the sensory attribute differences between two samples (sample with trilobatin and control without).

The control and sample contained 10% unsweetened cocoa powder in water (Dutch processed dark cocoa powder, commercially available from Hersheys), the sample additionally contained 0.0005% trilobatin.

The samples were served at room temperature.

Panelists found the samples with trilobatin to be less bitter but to keep their cocoa aroma. The alkaloid, alkaloid bitterness in the middle and towards the end of the temporal bitterness profile was markedly reduced, there was no bitter aftertaste, while an upfront, warm, woody rounded and smooth dark chocolate-like bitterness remained.

Example 2

Reduction of Alkaloid Bitterness in an Energy Drink with Trilobatin

The control and sample were caffeine containing energy drinks, the sample additionally contained 0.0005% trilobatin.

The tested caffeine containing energy drinks were sucrose-sweetened glucoronlactone and taurin containing Redbull™ energy drink, and Xenergy™ (Zyions Inc., USA) which is sucralose/Acesulfame-K sweetened and contains vitamin B, calcium, taurine and glucoronlactone.

All panelists found both energy drink samples with trilobatin to taste less bitter than the control. In particular bitterness in the middle of the temporal pattern is very effectively blocked. A slight bitter aftertaste remains which can be further blocked by combining with ingredients that particularly block bitterness in the late part of the temporal bitterness perception pattern.

Example 3

Reduction of Alkaloid Bitterness in Coffee with Trilobatin

The sample and control were instant coffee (Nescafe, Taster's choice) in water, the sample additionally contained 0.001% (10 ppm) trilobatin. All samples/controls were presented warm to the panelists.

All panelists found the sample to be less bitter than the control. The alkaloid caffeine bitterness in the middle and towards the end of the temporal bitterness profile was markedly reduced, there was no bitter aftertaste.

At higher concentrations, in particular at about 50 ppm, bitterness is masked at the same time the coffee flavor is suppressed; the effect starts at about 20 ppm, with up to 30 to 40 ppm still giving acceptable results. At about 50 ppm or more the coffee flavor is significantly affected.

Example 4

Reduction of Alkaloid Bitterness in Tea with Trilobatin

Sample and control were brewed black tea (tea bags, Lipton), the sample additionally contained 0.001% trilobatin which was added to the brewed tea.

Samples and controls were served warm.

Most panelists found the sample to be slightly less bitter than the control, some detected no difference or were not sure.

Example 5

Reduction of Caffeine-Bitterness with Trilobatin

The control and sample contained 0.02 or 200 ppm % caffeine in water, the sample additionally contained 0.000125 to 0.0020 trilobatin.

Panelists found that in the samples, caffeine bitterness was reduced at concentrations starting from 0.0005% (5 ppm) up to 0.0020 trilobatin (20 ppm), but not at 0.000125% (1.25 ppm) trilobatin when compared to the control.

Example 6

No Reduction of Tannin-Bitterness with Trilobatin

The control and sample contained 0.05%/500 ppm tannic acid in water. The samples additionally contained 0.000125 to 0.002% trilobatin.

The samples and the control were found to be similarly bitter, indicating that trilobatin does not mask tannin-derived bitterness.

Example 7

Reduction of Alkaloid Bitterness in Cocoa with HDG

A tasting panel of 5 to 8 panelists was asked to compare and record the sensory attribute differences between two samples (sample with HDG and control without).

The control and sample contained 10% unsweetened cocoa powder in water (Dutch processed dark cocoa powder, commercially available from Hersheys), the sample additionally contained 0.0020% (w/w) HDG.

The samples were served at room temperature.

Panelists found the samples with HDG to be less bitter but to keep their cocoa aroma. The purine alkaloid bitterness (theobromine, caffeine) in the middle was reduced, but there was a bitter aftertaste that remained. The upfront, warm, woody rounded and smooth dark chocolate-like bitterness remained.

Example 8

Determination of the Sweetness Detection Threshold of the Bitter Blocker Trilobatin The sweetness detection threshold of trilobatin was determined as detailed below in 1a, 1b and 1c. All examples were performed with sweet sensitive panelists able to detect at least 0.5% of sucrose or less, unless stated otherwise. The concentration detectable by the average consumer will be higher.

1a. Paired Comparison of 20-100 ppm Trilobatin Versus 0-1% Sucrose

Trilobatin (20 ppm, 60 ppm, 100 ppm) in water samples were evaluated for isointensity to sucrose solutions in a concentration of 0, 0.5 and 1% sucrose using a paired comparison method. Samples were paired and tasted left to right with rinsing (water) in between, by one panelist trained for sweetness detection. Once completing the sequence, the panelist ranked the pair of samples for sweetness then evaluated samples with respect to one another with the following descriptors (in ascending order): "significantly less sweet", "less sweet", "notably less sweet", "isosweet", "weakly sweeter", "sweeter", "notably sweeter", "significantly sweeter".

The trilobatin samples were compared to either 0%, 0.5%, or 1% sucrose solutions. The results are indicated in the table below.

| Trilobatin [ppm] | Taste of trilobatin samples compared to sucrose | Sucrose [% wt/wt] |
|---|---|---|
| 20 | isosweet | 0 |
| 20 | notably less sweet | 0.5 |
| 60 | weakly sweeter | 0 |
| 60 | less sweet | 0.5 |
| 100 | sweeter | 0 |
| 100 | isosweet | 0.5 |
| 100 | less sweet | 1 |

The 20 ppm solution of trilobatin had no detectable difference from 0% sucrose and was notably less sweet than 0.5% sucrose. The 60 ppm trilobatin sample was weakly sweeter than 0% sucrose and but was found to be less sweet than 0.5% sucrose, which is barely detectably sweet. Accordingly, the 60 ppm trilobatin sample was isosweet to 0.25% sucrose, or below the sweetness detection threshold, by interpolation. The 100 ppm trilobatin sample was sweeter than 0% sucrose and isosweet to 0.5% sucrose, which is weakly sweet.

1b. Isointensity of 100 ppm Trilobatin

The sensory evaluation was conducted using a ranking method. Samples at ambient temperature were randomly presented in 15 ml blind aliquots (unidentifiable by panelists). Panels consisted of 15 sweet sensitive subjects and samples were presented in 2 replications over 1 session. After tasting each sample, the mouth was rinsed thoroughly with water at ambient temperature prior to tasting the next sample.

Panelists were presented with 0.5%, 1%, 1.5% and 2% sucrose solutions in water and a fifth sample of 100 ppm trilobatin in water. Subjects were asked to rank the samples from low to high with respect to perceived sweet taste.

R-indices were calculated for 100 ppm trilobatin versus either 0.5%, 1%, 1.5% or 2% sucrose.

An R-index greater than the higher critical value means that the sweetness enhancer sample was significantly sweeter than the sucrose sample. An R-index from 50% to the upper critical value would mean that the sweetness enhancer sample had an equivalent sweetness to the compared sucrose sample. An R-index below the lower critical value (see table below) indicates that the sucrose sample was sweeter than the sweetness enhancer sample.

| sucrose solution [% wt/wt] | sample sweetness (trilobatin, 100 ppm) | R-index | Critical values [%] | p-value |
|---|---|---|---|---|
| 0.5% Sucrose | Isosweet | 44% | 35.39-64.61 | P > 0.05 |
| 1.0% Sucrose | Less sweet | 13% | 35.39-64.61 | P < 0.05 |
| 1.5% Sucrose | Less sweet | 0% | 35.39-64.61 | P < 0.05 |
| 2.0% Sucrose | Less sweet | 0% | 35.39-64.61 | P < 0.05 |

An R index of 44%, which is within the critical value range (35.39-64.61%), means the 100 ppm trilobatin in water sample was isosweet to 0.5% sucrose. An R index of 0-13%, which is below the lower critical value, means the sample was less sweet than either 1%, 1.5% and 2% sucrose. Thus, the 100 ppm trilobatin in water sample was perceived to be isointense to a 0.5% sucrose solution.

1c. Isointensity of 200 ppm Trilobatin

The sensory evaluation was conducted using the method described in example 1b. The panels consisted of 7 sweet sensitive panelists. Panelists were presented with 0.5%, 1%, and 1.5% sucrose solutions in water and a fourth sample of 200 ppm trilobatin in water. Panelists were asked to rank the samples from low to high with respect to perceived sweet taste.

200 ppm trilobatin in water was determined to be isosweet to 1% sucrose.

The sweetness detection threshold for individuals within the average consumer group varies from below 0.4% to 0.7% sucrose or more. All examples were performed with sweet sensitive panelists able to detect at least 0.5% sucrose or less. Extrapolating from examples 1a, b, and c, the concentration detectable by the average consumer will therefore be higher, and the average concentration near the sweetness detection threshold of the average consumer will be about 100 to 200 ppm.

Example 9

Determination of the Sweetness Detection Threshold of HDG

All examples were performed with sweet sensitive panelists able to detect at least 0.5% of sucrose or less, unless stated otherwise. The concentration detectable by the average consumer will be higher. The results were obtained using 20 panelists in two replications.

The sucrose concentration that tastes isointense in sweetness to HDG was determined using samples of 15 ppm and 20 ppm, each of which was directly compared to a sucrose sample (sucrose solutions of 0.5%, 1%, 1.5% and 2% concentration). Fifteen milliliters of each blinded sample was presented, at room temperature, in random order to 20 sweet sensitive panelists. In two replications (over 1 session), panelists were asked to rank the solutions, from least sweet to most sweet. The data was subjected to an R-index analysis. The results are indicated in the tables below.

| sucrose solution [% wt/wt] | sample sweetness (HDG, 15 ppm) | R-index | Critical values [%] | Significantly different (p < 0.05) |
|---|---|---|---|---|
| 0.5% Sucrose | sweeter | 85% | 37.26-62.74 | Yes |
| 1.0% Sucrose | less sweet | 31% | 37.26-62.74 | Yes |
| 1.5% Sucrose | less sweet | 10% | 37.26-62.74 | Yes |
| 2.0% Sucrose | less sweet | 1% | 37.26-62.74 | Yes |

| sucrose solution [% wt/wt] | sample sweetness (HDG, 20 ppm) | R-index | Critical values [%] | Significantly different (p < 0.05) |
|---|---|---|---|---|
| 0.5% Sucrose | Sweeter | 92% | 37.26-62.74 | Yes |
| 1.0% Sucrose | Isosweet | 51% | 37.26-62.74 | No |
| 1.5% Sucrose | Less sweet | 33% | 37.26-62.74 | Yes |
| 2.0% Sucrose | Less sweet | 4% | 37.26-62.74 | Yes |

15 ppm HDG was perceived to be significantly sweeter than a 0.5% sucrose sample (the calculated R-index value exceeds the critical values), but significantly less sweet than 1.0%, 1.5% and 2% sucrose samples (the calculated R-index values less than the critical values).

20 ppm HDG was perceived to be isointense to the sweetness of the 1.0% sucrose sample, significantly sweeter than 0.5% sucrose (the calculated R-index value was exceeds the critical value), and significantly less sweet than 1.5% and 2% sucrose (the calculated R-index values less than the critical values).

Further three small panel testings were performed. HDG samples were prepared in concentrations of 5 ppm, 10 ppm, 15 ppm, and 20 ppm in water. All the samples were coded (presented blind) and given to the panel in random order. The panel was also presented with sucrose solutions for comparison The panel was asked to taste each sample and rank the samples from the least sweet to most sweet. The results are indicated in the table below.

| Sample concentration (HDG in water) | Rank and taste | Isointensity to sucrose |
|---|---|---|
| 5 ppm | 1 - not sweet | 0% sucrose (water) |
| 10 ppm | 2 - very slightly sweet | 0.5% sucrose |
| 15 ppm | 3 - slightly sweet | 0.75% sucrose |
| 20 ppm | 4 - sweet | 1% sucrose |

The 5 ppm solution of HDG was found not to be sweet (below the sweetness detection threshold). The 10 ppm HDG was found to be very slightly sweet, isosweet to 0.5% sucrose. Thus the sweetness threshold of HDG detected by sweet sensitive individuals (which are more sensitive than the average consumer) is at about 10 ppm. The 15 ppm and 20 ppm samples were identified as slightly sweet and sweet (isosweet to 0.75% sucrose and 1% sucrose, respectively).

The invention claimed is:
1. A consumable composition, comprising
a) at least 10 mg/l of one or more bitter alkaloid selected from caffeine, theobromine, and theophylline, and
b) at least one bitter blocker selected from:
   trilobatin which is present in the consumable composition in a concentration of 3-200 ppm, and
   hesperitin dihydrochalcone 4"-beta-D-glucoside (HDG) which is present in the consumable composition in a concentration of 0.3-20 ppm, and wherein the bitter blocker is present in the consumable com- position at a level equal to or less than isosweet to 1% sucrose, and where the consumable composition is not chewing gum.

2. The consumable composition of claim 1 wherein the bitter blocker is trilobatin.

3. The consumable composition of claim 1 wherein the bitter blocker is hesperitin dihydrochalcone 4"-beta-D-glucoside (HDG).

4. The consumable composition according to claim 1, wherein one or more ingredients selected from the group consisting of: 4-(2,2,3-Trimethylcyclopentyl)butanoic acid, vanilla extracts, licorice extracts, glycyrrhizin, thaumatin, and mixtures thereof are also present.

5. The consumable composition according to claim 1 comprising one or more ingredients selected from the group consisting of:
one or more vitamins;
coffee or an extract thereof (*Coffea* spec.);
cocoa or an extract thereof (*Theobroma* spec.);
guarana or an extract thereof (*Paullinia cupana, P. crysan*, or *P. sorbilis*);
black tea or an extract thereof;
green tea or an extract thereof;
yerba mate or an extract thereof;
(*Camellia* spec. extracts);
Yaupon/Cassina extracts (*Ilex vomitoria*);
taurine;
*ginseng* or an extract thereof;
kola or an extract thereof (*Cola acuminata*);
carob or an extract thereof (*Ceratonia siliqua*);
maltodextrin;
inositol;
carnitine;
creatine;
glucuronolactone; and,
*ginkgo biloba* extract.

6. The consumable composition according to claim 1 wherein the said composition is a beverage comprising caffeine as a bitter alkaloid.

7. The beverage according to claim 6 which is selected from the group consisting of: a coffee beverage for hot consumption, a coffee beverage for iced consumption, a cocoa beverage for hot consumption, a cocoa beverage for iced consumption, a black tea beverage for hot consumption, a black tea beverage for iced consumption, a green tea beverage for hot consumption, a green tea beverage for iced consumption, a mate tea beverage for hot consumption, a mate tea beverage for iced consumption, and an energy drink for cold consumption.

8. The consumable composition according to claim 1 comprising trilobatin extracted from a botanical source optionally selected from: parts or leaves of *Lithocarpus polystachyus* (Chinese sweet tea) and, parts or leaves of an apple species, said apple species optionally being selected from *Malus trilobata*.

9. A method of blocking bitterness in a consumable composition, wherein the consumable composition comprises at least 10 mg/l of a bitter alkaloid, the comprising the step of:
admixing a bitter blocker selected from:
trilobatin which is present in the consumable composition in a concentration of 3-200 ppm, and
hesperitin dihydrochalcone 4"-beta-D-glucoside (HDG) which is present in the consumable composition in a concentration of 0.3-20 ppm, and wherein the bitter blocker is present in the consumable composition at a level equal to or less than isosweet to 1% sucrose, and where the consumable composition is not chewing gum.

10. The method of claim 9, wherein the bitter blocker is trilobatin extracted from a botanical source optionally from: parts or leaves of *Lithocarpus polystachyus* (Chinese sweet tea) and; parts or leaves of an apple species, said apple species optionally being selected from *Malta trilobata.*

11. A method of reducing the bitterness of a bitter alkaloid, while not imparting a perceptible sweetness in a consumable composition comprising the bitter alkaloid which method comprises the step of:
including within the composition a bitter blocker selected from:
trilobatin which is present in the composition in a concentration of 3-200 ppm, and
hesperitin dihydrochalcone 4"-beta-D-glucoside (HDG) which is present in the composition in a concentration of 0.3 to 20 ppm, and further wherein;
the bitter blocker is present in the consumable composition at a level equal to or less than isosweet to 1% sucrose, and where the consumable composition is not chewing gum.

12. A consumable composition according to claim 1, selected from: a food consumable, a beverage consumable, and a pharmaceutical consumable.

13. A method according to claim 9 wherein the bitter alkaloid is selected from: caffeine, theobromine, and theophylline.

14. A method according to claim 11, wherein the bitter alkaloid is selected from caffeine, theobromine, and theophylline.

15. A method according to claim 11, wherein the consumable composition is selected from: a food, a beverage, a nutraceutical, and a pharmaceutical.

16. A consumable composition according to claim 1 wherein the at least one bitter blocker is trilobatin which is present at a concentration of 3-150 ppm.

17. A consumable composition according to claim 16 wherein the at least one bitter blocker is trilobatin which is present at a concentration of 3-100 ppm.

18. A consumable composition according to claim 1 wherein the at least one bitter blocker is HDG which is present at a concentration of 0.3 to 10 ppm.

19. A consumable composition according to claim 1 wherein the bitter alkaloid is present at a concentration of at least 100 mg/l.

20. A consumable composition according to claim 1, wherein the consumable composition is a food product selected from the group consisting of:
cereal products, rice products, tapioca products, sago products, baker's products, biscuits, bread, breakfast cereal, cereal bar, energy bars/nutritional bars, granola, cakes, cookies, crackers, donuts, muffins, pastries, chocolates, ices, honey products, treacle products, yeast products, baking-powder, salt products, spice products, savory products, mustard products, vinegar products, sauces (condiments), tobacco products, cigars, cigarettes, processed foods, cooked fruits, vegetable products, meat, meat products, jellies, jams, gelatins, fruit sauces, egg products, milk products, dairy products, yoghurts, cheese products, butter, butter substitute products, milk substitute products, soy products, edible oils, fat products, food extracts, plant extracts, meat extracts, and condiments.

21. A consumable composition according to claim 1, wherein the consumable composition is a dairy product, a dairy-derived product or a dairy alternative product selected from the group consisting of:
whole milk, skim milk, condensed milk, evaporated milk, reduced fat milk, low fat milk, nonfat milk, and milk solids, cultured milk product, cultured and noncultured dairy-based drinks, cultured milk product cultured with *lactobacillus*, yoghurt, yoghurt-based beverage, smoothy, lassi, milk shake, acidified milk, acidified milk beverage, buttermilk, kefir, milk-based beverage, milk/juice blend, fermented milk beverage, ice cream, dessert, frozen yoghurt, soy milk, rice milk, soy drink, and rice milk drink.

22. A consumable composition according to claim 1, wherein the consumable composition is a water-based consumable composition selected from the group consisting of:
aqueous drink, enhanced/slightly sweetened water drink, carbonated beverage, non-carbonated beverage, soft drink, non-alcoholic drink, mineral water, aerated water, alcoholic drink, beer, fruit drink, juice, fruit juice, vegetable juice, coffee, artificial coffee, tea, black tea, green tea, oolong tea, herbal tea, cocoa (water-based), cocoa (milk-based), cocoa (soy-based), tea-based drink, coffee-based drink, cocoa-based drink, syrup, frozen fruit, frozen fruit juice, water-based ice, dairy ice, fruit ice, sorbet, and beverages formed from botanical materials (whole or ground) by brewing, soaking or otherwise extracting, and beverages formed by dissolving instant powders or concentrates including coffee beans, ground coffee, instant coffee powder, cocoa beans, cocoa powder, instant cocoa powder, tea leaves and instant tea powder.

23. A consumable composition according to claim 1, wherein the consumable composition is a nutraceutical composition or is a pharmaceutical composition.

24. A consumable composition according to claim 23, wherein the consumable composition is a tablet, a lozenge, a drop, an emulsion, an elixir or a syrup.

25. A consumable composition according to claim 1, wherein the consumable composition is at an acidic pH.

26. A consumable composition according to claim 25, wherein the consumable composition is at a pH in the range of about 2.6-3.

* * * * *